US006652594B2

(12) United States Patent
Francis et al.

(10) Patent No.: US 6,652,594 B2
(45) Date of Patent: Nov. 25, 2003

(54) RESORBABLE IMPLANT MATERIALS

(75) Inventors: Ralph T. Francis, New Brighton, MN (US); Qing Hong Zhao, Andover, MN (US); Amy DeSmith, Circle Pines, MN (US); B. Nicholas Oray, Woodbury, MN (US)

(73) Assignee: Synovis Life Technologies, Inc., St. Paul, MN (US)

( * ) Notice: Subject to any disclaimer, the term of this patent is extended or adjusted under 35 U.S.C. 154(b) by 0 days.

(21) Appl. No.: 10/099,425

(22) Filed: Mar. 14, 2002

(65) Prior Publication Data

US 2002/0138152 A1 Sep. 26, 2002

Related U.S. Application Data

(63) Continuation of application No. PCT/US00/25234, filed on Sep. 14, 2000, which is a continuation of application No. 09/396,279, filed on Sep. 15, 1999, now Pat. No. 6,312,474.

(51) Int. Cl.$^7$ ............................... A61F 2/36; A61F 2/10
(52) U.S. Cl. .................. 623/23.72; 623/15.12
(58) Field of Search .......................... 623/23.72, 23.73, 623/23.74, 23.75, 23.76, 13.17, 14.13, 15.11, 15.12

(56) References Cited

U.S. PATENT DOCUMENTS

| 3,991,184 A | 11/1976 | Kludas et al. ............... 424/177 |
| 4,915,113 A | 4/1990 | Holman |
| 5,085,629 A | 2/1992 | Goldberg et al. |
| 5,306,286 A | 4/1994 | Stack et al. |
| 5,376,112 A | 12/1994 | Duran |
| 5,411,965 A | 5/1995 | Reid et al. |
| 5,413,798 A | 5/1995 | Scholl et al. |
| 5,447,922 A | 9/1995 | Lawrence et al. |
| 5,503,638 A | 4/1996 | Cooper et al. |
| 5,549,628 A | 8/1996 | Cooper et al. |
| 5,575,803 A | 11/1996 | Cooper et al. |
| 5,752,965 A | 5/1998 | Francis et al. |
| 5,783,214 A | 7/1998 | Royer |
| 5,830,915 A | 11/1998 | Pikul et al. |
| 5,837,278 A | 11/1998 | Geistlich et al. |
| 5,837,533 A | 11/1998 | Boutin |
| 5,895,420 A | 4/1999 | Mirsch, II et al. |
| 6,187,048 B1 | 2/2001 | Milner et al. |
| 6,268,361 B1 * | 7/2001 | Palkowitz ................. 514/231.2 |
| 6,274,635 B1 * | 8/2001 | Travis ......................... 514/718 |
| 6,280,760 B1 * | 8/2001 | Meyer et al. ................ 424/423 |
| 6,312,474 B1 * | 11/2001 | Francis et al. ............ 623/23.72 |

FOREIGN PATENT DOCUMENTS

| EP | 0987942 | 8/1998 |
| WO | WO 99/48540 | 3/1999 |

OTHER PUBLICATIONS

Ashammaki, N.A., "Neomembranes: A Concept Review with Special Reference to Self–Reinforced Polyglycolide Membranes", J. Biomed. Mater., Res., 33: 297–303; 1996.
Hanbrough, J.F., et al., "Composite Grafts of human keratinocytes Growth On a Polyglactin Mesh–Cultured Fibroblast Dermal Substitute Function as a Bilayer Skin Replacement in Full=Thickness Wounds on Athymic Mice", J. Burn Care Rehab., 14: 485–494; 1993.
Gratzer, P.F., et al., "Solvent environment modulates effects of glutaraldehyde Crosslinking on tissue–derived biomaterials", J. Biomed. Mater. Res., 31: 533–543; 1996.
Sung, H–W., et al., "In vitro study of enzymatic degradation of biological tissues fixed by glutaraldehyde or epoxy compound", J. Biomater. Sci. Polymer Edn., 8: 587–600; 1997.
Sung, H.W., et al., "Effects of various chemical sterilization methods on the croslinking and enzymatic degradation characteristics of an epoxy–fixed biological tissue", J. Biomed. Mater. Res. 37:376–383 (1997).
Tu, R. et al., "Fixation of bioprosthetic tissues with monofunctional and multifunctional polyepoxy compounds", J. Biomed. Mater. Res., 28:677–684 (1994).

* cited by examiner

Primary Examiner—Corrine McDermott
Assistant Examiner—Hieu Phan
(74) Attorney, Agent, or Firm—Fredrikson & Byron, P.A.

(57) ABSTRACT

A non-crosslinked, decellularized and purified mammalian tissue (e.g., bovine pericardium) having particular use as an implantable resorbable material. The material is treated by alkylating its primary amine groups in a manner sufficient to reduce the antigenicity of the tissue, permitting the treated tissue to be used in vivo and without crosslinking, and in turn, permitting it to be resorbable. The material can be used in surgical repair of soft tissue deficiencies for a certain period of time while the implant itself is gradually remodeled or absorbed by the host. Also provided are a method of preparing such a material, as well as a method of using such a material for surgical repair.

24 Claims, No Drawings

RESORBABLE IMPLANT MATERIALS

CROSS REFERENCE TO RELATED APPLICATIONS

The present application is a continuation of and claims priority to International Application No. PCT/US00/25234 (published as International Publication No. WO 01/19423), filed Sep. 14, 2000 and designating the United States, which in turn is a continuation of patent application having U.S. Ser. No. 09/396,279, filed Sep. 15, 1999, now U.S. Pat. No. 6,312,474 the entire disclosure of which is incorporated herein by reference.

TECHNICAL FIELD

The invention relates to materials for the use as implants within the body, and in particular, to resorbable and remodelable materials for such use.

BACKGROUND OF THE INVENTION

Various resorbable (occasionally referred to as absorbable or "remodelable") materials presently exist for use in prosthetic applications, e.g., as patches, implants and/or as components of prosthetic devices.

Synthetic resorbable materials made from the polyesters, polylactide and polyglycolide, for example, have found use in various fields of medicine (See, e.g., Ashammaki, N. A., J. Biomed. Mater. Res., 33: 297–303; 1996). Versions of these materials exist commercially under the tradenames Vicryl® (Ethicon, Inc.) and Dexon® (Davis & Geck, Inc.). The gradual decomposition of these polymers is facilitated by hydrolysis, and catalyzed by biochemical action of the host tissues (Hanbrough, J. F., et al., J. Burn Care Rehab., 14: 485–494; 1993). These materials may be produced as membranes or as woven mesh in the case of producing resorbable suture.

While synthetic resorbable materials are a rather recent phenomenon, collagenous materials have been used as prosthetic grafting for many years; as in the case of lyophilized human dura, dating back to 1954. As a common practice for several years, such collagenous materials have been crosslinked with an agent such as glutaraldehyde, in order to diminish the antigenicity of a xenograft while increasing its resistance to enzymatic degradation produced by host tissue responses (Gratzer, P. F., et al., J. Biomed. Mater. Res., 31: 533–543; 1996). Polyepoxy compounds have also been used for such purposes, however are more stable with regard to the resulting alkylated amines in the collagen (Sung, H-W., et al., J. Biomater. Sci. Polymer Edn., 8: 587–600; 1997). While crosslinked tissues work well as long-term implants, they are not resorbable and as such, do not promote host tissue remodeling, or in turn, the eventual replacement of a graft by the body itself.

Aesculap AG & Co. (B. Braun Surgical) offers products under the tradename Lyoplant®, in the form of a bovine pericardium-based resorbable replacement for dura mater. Lyoplant® is produced by a process that involves mechanical removal of adherent fat and connective tissue, chemical treatment to inactivate enzymes and potential pathogens, freeze-drying, cutting to various sizes, packaging and terminal sterilization with ethylene oxide. The product is indicated to be used for covering cerebral and cerebellar dural defects, for decompressive duraplasty in cases of increased intracranial pressure, for covering spinal dural defects and for spinal decompressive duraplasty. This material has been observed to be fully remodeled within one year after implant.

Tutogen Medical, Inc. provides processed pericardium products under the tradename Tutoplast®, in the form of a solvent-dehydrated, gamma-irradiated preserved human pericardium. The processing of Tutoplast® tissue involves thorough cleaning, processing, dehydration and preservation. The process is said to leave no deleterious residue and minimizes antigenic potential. Collagenous connective tissue with multidirectional fibers retains the mechanical strength and elasticity of native pericardium, while providing the basic formative structure to support replacement by new endogenous tissue. This tissue is indicated for use in a variety of surgical applications, including duraplasty (as a substitute for human dura mater), and in abdominal, urological, opthalmological, and vascular surgery. The absorption process and reformation of endogenous tissue begins one to two days after implantation and continues for weeks, months, or years, depending on the size of the graft and the responsiveness of the graft site. Mentor Corporation has entered a strategic alliance with Tutogen Medical, Inc., to use the Tutoplast® technology to manufacture resorbable slings for urinary incontinence (Suspend™).

A variety of other uses of resorbable materials are described in the patent literature. See, for instance, U.S. Pat. No. 5,895,420 (Mirsch, II, et al., "Bioresorbable Heart Valve Support"), which relates to bioprosthetic heart valve stents that are fashioned of resorbable materials. Such stents may be configured as sheaths or frames contoured to the shape of a valvular graft. The stents are eventually resorbed by the patient, leaving a functional "stentless" valve with improved hemodynamic characteristics compared to stented valve implants.

Various other resorbable materials have been suggested or proposed for use with vascular of non-vascular implants. For example, Goldberg et al., U.S. Pat. No. 5,085,629 discloses a biodegradable infusion stent for use in treating ureteral obstructions. Stack, et al., U.S. Pat. No. 5,306,286 discloses an absorbable stent for placement within a blood vessel during coronary angioplasty. Duran, U.S. Pat. No. 5,376,112 discloses an annuloplasty ring to be implanted into the heart to function together with the native heart valve.

In another aspect, U.S. Pat. No. 5,837,278 (Geistlich, et al., "Resorbable Collagen Membrane for Use in Guided Tissue Regeneration"), describes the use of a collagen-containing membrane in guided tissue regeneration. The patent provides a resorbable collagen membrane for use in guided tissue regeneration wherein one face of the membrane is fibrous thereby allowing cell growth thereon and the opposite face of the membrane is smooth, thereby inhibiting cell adhesion thereon.

Finally, see U.S. Pat. No. 5,413,798 (Scholl, et al.) which describes a process for treating bovine pericardial tissue to increase resistance to biological degradation by wet-chemical processing. The use of the tissue is exemplified in the form of an implant which, after three and six months post implantation, was well integrated so that it was no longer distinguishable from autochthonous dura (revitalized by fibrocytes and traversed by blood vessels in the marginal zones). The inner side of the implant is coated with the same cell type as the autologous dura.

On yet another topic, certain articles describe basic research directed to studying the effect of alkylating agents on materials such as collagen. See, for example, Sung, H. W., et al., J. Biomed. Mater. Res. 37:376–383 (1997) and Tu, R. et al., J. Biomed. Mater. Res., 28:677–684 (1994). To the best of Applicants' knowledge, however, no such reference suggests the manner in which such materials might be used in vivo, nor in turn, do they address the question of whether such materials can be tolerated, let alone resorbed and remodeled, by the body.

The present assignee is recognized as a leader in the development and manufacture of pericardium based materials. See, for instance, U.S. Pat. Nos. 5,752,965; 5,575,803; 5,549,628; 5,503,638; and 4,915,113 and International Application No. US98/25674, the disclosures of each of which are incorporated herein by reference. Generally, the pericardium materials are crosslinked, e.g., using glutaraldehyde, and hence are typically considered non-resorbable. Such materials have been used in a variety of applications, including as patches, suture and staple line buttress members, and pledgets.

SUMMARY OF THE INVENTION

The present invention provides a non-crosslinked, decellularized and purified mammalian tissue (e.g., bovine pericardium) having particular use as an implantable material in a manner that is both resorbable and remodelable. The material is prepared by alkylating the primary amine groups of natural tissue in a manner sufficient to reduce the antigenicity of the tissue, and in turn, to an extent that permits the treated tissue to be used in vivo and without crosslinking, thereby permitting it to be resorbable.

The material can be used, for instance, in surgical repair of soft tissue deficiencies, for a period of time, while the implant itself is gradually remodeled or absorbed by the host. In a related aspect, the invention provides a method of preparing such a material, as well as a method of using such a material for surgical repair. As used herein with respect to a material of the present invention, the word "resorb" and inflections thereof will refer to a material that, once implanted in vivo, is absorbed by the body over time and without undue deleterious effects on or within the body itself. The word "remodel" and inflections thereof, as used with regard to a material of the present invention, will refer to a resorbable material that is adapted, e.g., by virtue of its location and method of implantation within the body, to encourage and/or permit the body to replace some or all of the structure and/or function of the implant with newly formed natural tissue. While not intending to be bound by theory, at least in some embodiments of the present invention, remodeling appears to occur by gradual bodily processes in which substantial portions of the implant material are gradually resorbed, while an inherent fibrous network of the implant is retained at the site. The network, in turn, is used by the body as essentially scaffolding for the generation of new tissue or tissue components.

In a preferred embodiment, the invention provides a resorbable implantable material comprising a non-crosslinked, decellularized and purified mammalian tissue having most of its free amine groups alkylated. In a particularly preferred embodiment, the tissue is selected from the group consisting of pericardium, peritoneum, fascia lata, dura mater, dermis and small intestinal submucosa, and the material has been alkylated by an alkylating agent selected from the group consisting of 1,2-epoxy-R compounds where R is an alkyl group up to 6 carbon atoms. Such a material can be provided in any suitable form, e.g., as flat or textured sheets or strips, and can be adapted for use in a variety of surgical applications, including those selected from the group consisting of duraplasty, thoracic, abdominal, urological, opthalmological, cardiac, and vascular surgery.

DETAILED DESCRIPTION

A tissue of the present invention can be obtained from any suitable source including mammalian sources, e.g., in the form of collagenous connective tissue with three dimensional intertwined fibers. Such tissues generally include serous and fibro-serous membranes. In a particularly preferred embodiment, the tissue source is selected from bovine pericardium, peritoneum, fascia lata, dura mater, dermis, and small intestinal submucosa. In a further preferred embodiment, the tissue is bovine pericardium, and is treated using a method as described herein to provide the treated tissue with an optimal combination of biocompatability, thickness, and other physical and physiological properties.

Tissues of the present invention can be provided from dura mater, for instance, for use in neurosurgical applications. Collagenous connective tissue with three dimensional intertwined fibers, when treated in the manner described herein, retains the multidirectional and mechanical strength of native dura matter, while providing the basic formative structure to support replacement by new endogenous tissue.

While it is desirable to reduce or eliminate antigenic properties of xenografic or even allografic tissue-based material to be implanted into a body, if the body's absorption and/or remodeling of the material are desired, crosslinking cannot be performed. In order to specifically perform such modification of a collagen-based material, a monofunctional reagent is therefore used. The reagent is "monofunctional" in that it is adapted to react with, and therefore terminate or "cap" the available amine functionalities of tissue proteins, but will not further react with adjacent groups. An optimal reagent of this invention, therefore, is preferably a relatively small and structurally simple compound that, upon reaction with protein groups such as amines, will bind to those groups but will not otherwise alter the biological properties of the collagen matrix to an extent that renders the tissue unsuitable for its intended use.

In a particularly preferred embodiment, a tissue of the present invention is treated by a process that includes alkylating a major percentage of its available amine groups to an extent sufficient to permit the tissue to be implanted and used in vivo. Preferably a tissue is processed by alkylating its amines to an extent sufficient to react 80% or more, preferably 90% or more, and most preferably 95% or more of the amine groups originally present. The efficacy and extent of alkylation can be determined by a variety of means, as described herein, including the use of a ninhydrin-based assay ("amine index") to determine a comparative level of amine groups, before and after treatment (see, e.g., Sung H-W, et al. Art Org., 21: 50–58; 1997. Sung, H-W, et al., J. Biomed. Mater. Res. 33: 177–186. 1996). Preferably the efficacy and extent of the alkylation process is further assessed by determining unreacted amounts in the batch incubation of the alkylating agent used.

Preferred alkylating agents can be used, for instance, at a pH of between about 9 and about 11, and at a concentration of between about 2% (v/v) and about 5% (v/v), by exposing the tissue to a solution containing the agent for at least 48 hours.

Preferred alkylating agents include small and reactive amine alkylating agents, such as formaldehyde, and 1,2-epoxy compounds. The epoxy agents offer an advantage over formaldehyde in that they tend to produce more stable adducts in their reactions with amines (Sung, H-W., et al., Biomater., 17: 2357–2365; 1996). 1,2-epoxy agents can react with a primary amine at alkaline pH to produce an extremely stable 2-hydroxy secondary amine. However, an aldehyde such as formaldehyde reacts with a primary amine to produce a marginally unstable, reversible double-bonded aldimine (Girardot, J.-M. and Girardot, M-N., J. Heart Valve Dis., 5: 518–525; 1996).

Of the various monofunctional 1,2-epoxy agents, propylene oxide ("PO") is particularly preferred since it possesses properties that render its inclusion into a material process simple, yet effective. Propylene oxide (epoxypropane) has been used for several years as a sterilant, mostly in a gaseous state, although at room temperature, it exists as a liquid (Hart, A. and Brown, W., Appl. Microbiol., 28: 1069–1070; 1975). Many years ago, PO was revealed to directly modify carboxylic, thiol, phenolic and amine groups of proteins under certain conditions (Fraenkal-Conrat, H., J. Biol. Chem., 154: 227–238; 1944). As has been demonstrated with other epoxides, propylene oxide reacts predominantly with amines at alkaline pH. Collagen swells at alkaline pH rendering it more accessible to be alkylated with a water-soluble agent such as propylene oxide.

Another preferred monofunctional epoxy reagent for use in the present invention is methyl glycidyl ether, as is produced by the Nagase Corp. of Osaka, Japan and sold under the product name Denacol® EX-131. This product has a low molecular weight, is water-soluble and was shown to be a more potent alkylator of porcine pericardium than formaldehyde (Sung, H-W., et al., J. Biomed. Mater. Res., 35: 147–155; 1997).

In addition to the "amine index", another test may be used to confirm tissue modification by an amine alkylating agent. The denaturation (shrink) temperature ($T_d$) is often used to verify the crosslinking of collagen by an agent such as glutaraldehyde. It is typically observed that upon chemical crosslinking, the $T_d$ increases significantly, apparently due to increased stabilization of the hydrogen bonds present in the collagen. In contrast, upon alkylation with a monofunctional agent such as propylene oxide, the $T_d$ decreases significantly. This phenomenon is believed to occur due to branching of the collagen polymer by the action of the alkylating agent and the subsequent alteration of the collagen matrix (Tu, R., et al., J. Biomed. Mater. Res., 28: 677–684; 1994).

In a preferred embodiment, a tissue of the present invention is also treated with a base such as sodium hydroxide (NaOH), in order to further lessen the already minimal possibility of Bovine Spongiform Encephalopathy (BSE) transmission. Histological analyses of NaOH-treated tissue (pericardium, for example) reveals virtually complete decellularization due to this treatment. Since the cellular component of tissue is known to contain the vast majority of the antigen load (Courtman, D. W., et al., J. Biomed. Mater. Res., 28: 655–666; 1994), decellularization treatment with NaOH can complement the use of an alkylating agent in reducing antigenicity.

A tissue of the present invention can be used to fabricate a prosthetic article having any suitable shape or configuration, and in any suitable dimensions for its intended use. For instance, the tissue can be provided and packaged in a flat configuration (e.g., sheet or tape-like), with either or both major surfaces thereof being optimally textured or modified (e.g., by the covalent attachment, entrapment, and/or adsorption of biologically active factors, lubricious agents, antimicrobial agents and the like).

In a preferred embodiment, a process of the present invention includes the steps of:

a) obtaining pericardium from a suitable (e.g., USDA-approved) source, b) cleaning the tissue and optionally, and preferably, treating the tissue, e.g., in order to decellularize it and/or to reduce/eliminate potential BSE infectivity, c) alkylating the tissue (e.g., hydroxypropylation using propylene oxide) to cap a major percentage of available (e.g., potentially reactive) amine groups, and optionally, d) final processing, including one or more of the following steps: washing, drying, sterilizing and packaging the tissue.

Natural tissues suitable for use in the process of this invention preferably meet stringent specifications during donor screening and laboratory testing to reduce the risk of transmitting infectious disease. Processing of tissue involves a strict, quality-controlled procedure, which involves thorough cleaning, processing, dehydration and preservation. The process leaves no deleterious residue and minimizes antigenic potential. Sterilization is preferably achieved with the use of gamma or electron beam radiation (typically 2.5 Mrad) or ethylene oxide gas.

A treated tissue of the present invention is indicated for implantation with a spectrum of indications. Collagenous connective tissue of this sort, having multidirectional fibers, is able to retain a substantial amount of the mechanical strength and elasticity of native pericardium, while providing the basic formative structure in situ to support replacement by new endogenous tissue. This tissue is indicated for use in a variety of surgical applications, including duraplasty (as a substitute for human dura mater), and in thoracic, abdominal, urological, opthalmological, cardiac and vascular surgery.

Implantation should be avoided into areas with active or latent infection or signs of tissue necrosis, as well as into areas with compromised circulation or in any disorder that would create an unacceptable risk of post-operative complications.

The tissue can be packaged using conventional means, such that the tissue and package contents remain sterile and non-pyrogenic as long as the package is not opened and/or damaged. The graft must be used before the expiration date. Those skilled in the appropriate art will appreciate the manner in which appropriate placement and fixation of the tissue in situ can be critical factors in avoiding potentially adverse effects on the graft service life. A tissue of this invention can be prepared and packaged in various sizes (e.g., thickness, length and width). The dimensions of tissue used should correspond to the size of the respective defect.

Once implanted, the absorption process and reformation of endogenous tissue begins one to two days after implantation and continues for weeks, months, or years, depending on the size of the graft and the responsiveness of the graft site. It is recommended that, if packaged in a dry or dehydrated condition, the tissue be rehydrated prior to use for about 2 to about 30 minutes, depending on the consistency desired, using aseptic/sterile technique. The surgeon should also monitor the effect of rehydration by visual inspection, both in the course of rehydration and while cutting and shaping the graft. Implantation should be performed in such a way that the free edges of the implant do not extend into areas where the possibility of adhesion may present a problem.

Absorbable or nonabsorbable suture material, glue, etc. can be used to fix the tissue in place. For a continuous suture, absorbable suture material and round atraumatic needles are recommended, while suture gauge depends on the surgical indication. The suture should be located two to three millimeters from the edge of the graft. Better results are obtained by doubling the section at suture sites that are under moderate to high stress.

Tissues of the present invention provide a variety of features and advantages, including the fact that they are immediately available for surgery and can save valuable operating room time. Moreover, there is no secondary surgery site and less stress for the patient; which can result in less time under anesthesia, no donor site pain or morbidity, and less cost. Since the tissues can be made available in a wide range of sizes, the surgeon can choose the size needed, leading to minimal waste. As with all biological products, it is not possible to provide an absolute guarantee of freedom from contaminating infectious diseases such as hepatitis, Creutzfeld-Jakob Disease (CJD) or Bovine Spongiform Encephalopathy (BSE). Processing treatments, such as the use of NaOH in the cases of CJD and BSE, have shown to be capable of reducing the risk of any transmission, and are particularly useful in combination with strict donor screening and laboratory testing. Treated tissues of the present invention can be stored in a clean, dry environment and at controlled temperatures between 4° C. and 30° C. (59° to 86° F.).

TEST PROCEDURES

Collagenase Assay

The enzyme class referred to as collagenase has been used for several years in studying its effects on collagenous biomaterials. Bacterial collagenase, e.g., from *Clostridium histolyticum*, can be used as an accurate predictor of the propensity and rate of resorption of a material by a mammalian host (Yannas, I. V., et al., J. Biomed. Mater. Res., 9: 623–628; 1975). Since modification of collagen by a crosslinking agent results in greatly diminished susceptibility to the action of collagenase, it is important that such modification not be performed on tissue to be resorbed. The mechanism by which crosslinking hinders the activity of collagenase is not completely understood. Surprisingly, applicants have found that bacterial collagenase is in fact able to degrade treated (alkylated) tissues of the present invention. Thus, tissue alkylated by an agent such as PO possesses pertinent and functional properties, and the collagenase assay remains a useful tool for confirming the utility of thus-treated tissue.

The collagenase assay is a ninhydrin-based assay for the indication of soluble collagen peptides produced by the action of the collagenase enzyme, and can be performed as follows:

1. Weigh out tissue in the range of 25–30 milligrams.
2. Add 3.0 milliliters of collagenase solution [0.01 mg/ml Collagenase enzyme (Sigma, type 1A) in 50 mM N-tris [hydroxymethyl]methyl-2 aminoethane sulfonic acid ("TES") buffer with 25 mM calcium chloride, pH 7.4–7.5].
3. Incubate at 37° C. for 24 to 96 hours.
4. At allotted timepoints, incubate 100 µl of collagenase solution and 1.0 ml ninhydrin solution [one part 4% (w/v) ninhydrin in ethylene glycol monoethyl ether to one part 200 mM citric acid, 0.16% (w/v) stannous chloride, pH 5.0] at 95–100° C. for 30 minutes.
5. Cool tubes at room temperature.
6. Add 250 µl of collagenase sample to 1.0 ml 50% isopropanol.
7. Vortex and read absorbance at 570 nm.
8. The absorbance at 570 nm is divided by the weight of the piece of tissue to give the OD/mg.

The OD/mg is the value for the amount of collagen peptides that has been degraded by the action of the collagenase enzyme.

The results of the collagenase assay are determined by comparing the sample with both positive (untreated) and negative (glutaraldehyde crosslinked) control samples.

Amine Index

The amine index can be defined as the percentage of initially available amines that have been modified (and thereby rendered substantially nonreactive in vivo) by reaction with amine reagents. Such modification will render the amine unable to produce "Ruhemann's purple" when introduced to ninhydrin, and the relevant assay can be performed as follows:

1. 200 µl of DI water were added to 25–30 milligrams of tissue.
2. Add one milliliter of ninhydrin solution to each tube.
3. Incubate tubes at 95–100° C. for 30–35 minutes.
4. Cool tubes at room temperature.
5. Add 250 µl of sample to one milliliter of 50% isopropanol solution.
6. Vortex and read absorbance at 570 nm.
7. The amine index is calculated.

In order to calculate the percentage of original amines modified, the following formula is used:

$$\text{Amine Index } (\%) = \frac{[^*\text{Control } (OD/\text{mg}) - \text{Sample } (OD/\text{mg})]}{\text{Control } (OD/\text{mg})} \times 100$$

The OD/mg is found by dividing the OD @ 570 by the weight of the piece of tissue. * The control is unmodified tissue.

Assay for Quantitation of Unreacted Alkylating Agent

The purpose of this assay is to confirm that although 100% amine alkylation is typically not attained, it is not due to the lack of adequate alkylating agent. In essence, this assay is used to confirm that detectable levels of alkylating agent remain in the incubation solution upon exhaustive exposure to the tissue. Upon exposure of tissue to an alkylating agent, the agent solution can be sampled in order to quantitate the percentage remaining. This test is in part performed for the purpose of assessing the efficiency of alkylation. Quantitation is assessed using a standard curve.

1. 10 mM Glycine solution is prepared by adding 0.0375 grams of glycine to 50 milliliters of 0.2 M carbonate ($Na^{+2}$) buffer.
2. Propylene oxide (PO) standards are prepared (e.g., ranging from 0.5% PO to 5% PO). The standards are prepared by adding the correct amount of PO to the carbonate buffer for a total of five milliliters.
3. Add 1 milliliter of the glycine solution to labeled test tubes.
4. Add 1 milliliter of each PO standard to the labeled test tube.
5. Vortex to mix and allow to react for 24 hours at room temperature.
6. After 24 hours, 50 µl of each standard was added to one milliliter of ninhydrin solution.
7. Incubate tubes at 95–100° C. for 30 minutes.
8. Cool tubes at room temperature.
9. Add 250 µl of standard to one milliliter of 50% isopropanol solution.
10. Vortex and read absorbance at 570 nm.

The samples containing unknown propylene oxide concentrations are assessed using the method above. Once the propylene oxide standard curve is plotted, the samples containing unknown propylene oxide concentrations can be estimated using the standard curve.

Moisture Content

Moisture content was analyzed on a Mettler-Toledo HG53 Halogen Moisture Analyzer. A temperature setting of 200° C. was used. Results are recorded in % moisture content.

Denaturation (Shrink) Temperature

Denaturation temperature is the temperature at which the collagen denatures. The test was performed on the Chem-Dyne MC1000 tensile testing system. The denaturation temperature was measured using a 30 gram preload in a bath of water at steadily increasing temperature. Results are expressed in ° C.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments.

EXAMPLE 1

Bovine pericardial sacs were harvested from USDA inspected healthy cows, minimum age of 12 months. Fresh pericardium was obtained and sent through a series of rinses, followed by a final ice cold water rinse. The tissue was cleaned of extraneous tissue, and used fresh or stored at −20° C. The following general procedures were used to prepare treated tissue according to the present invention. All test procedures are performed at 20–25° C.

NaOH & Neutralization
1. Weigh out 40–45 grams of bovine pericardium.
2. Place pericardium into one liter of 1.0 M NaOH (40 grams of NaOH in one liter of DI water) for 60–65 minutes. Take a sample for pH measurement at the end of soak.
3. Decant NaOH; gently squeeze tissue and place in two liters of filtered DI water for 15–20 minutes.
4. Decant DI water and place tissue in two liters of citrate buffer (28 grams of sodium citrate and 2.0 grams of citric acid in two liters of DI water) for 60–65 minutes. Take a sample for pH measurement at the end of soak.
5. Decant citrate buffer, gently squeeze tissue and place tissue in another two liters of DI water for 30–35 minutes.

Alkylation of Tissue
1. Prepare 5% Propylene Oxide solution (50 milliliters of propylene oxide in 950 milliliters of 0.2 M carbonate buffer, pH 10.5–10.6).
2. Place NaOH-treated tissue in propylene oxide solution.
3. Mix on platform shaker for 72–96 hours.
4. Remove tissue from solution and place in 1.5 liters of DI water for 24 hours.

After hydroxypropylation of tissue, the amine index and the quantitation of unreacted 20 alkylating agent assays are performed to verify sufficient alkylation and PO. The tissue was transferred onto wire mesh racks and dried in a Virtis Genesis vacuum dryer at 115 mtorr.

Results

TABLE 1

Collagenase Activity.
The table below provides the results of a collagenase assay when resorbable tissue prepared in the manner described herein was incubated in 0.01 mg/ml collagenase for 24–96 hours.

| Tissue | 24 hr OD/mg | 48 hr OD/mg | 72 hr OD/mg | 96 hr OD/mg |
|---|---|---|---|---|
| Untreated | 0.319 | 0.423 | 0.459 | 0.481 |
| NaOH | 0.502 | 0.689 | 0.784 | 0.874 |
| NaOH/PO | 0.674 | 0.684 | 0.822 | 0.973 |

OD/mg is the relative value for the amount of collagen that has been degraded by the action of the collagenase enzyme. It can be seen that each of the tissues, including the alkylated tissue of this invention, are susceptible to collagenase digestion, indicating the likelihood that they would be resorbed within the body.

TABLE 2 pH Dependence
The following table provides the amine index results of NaOH/PO-treated tissue when incubated in a 5% PO solution at two different pHs.

| Tissue | Amine Index @ pH 9.5 | Amine Index @ pH 10.5 |
|---|---|---|
| NaOH/PO | 84.76% | 96.29% |

It can be seen that, under the experimental circumstances involved, the extent of alkylation could be increased at higher pH.

TABLE 3

Time Dependence
The following table provides the amine index results of NaOH/PO-treated tissue when incubated in a 5% PO solution for a period of time at a pH of 10.5.

| Tissue | 72 hr PO incubation | 96 hr PO incubation |
|---|---|---|
| NaOH/PO | 93.95% | 96.29% |

It can be seen that there is a slight increase in alkylation, even in the period from 72 to 96 hour incubation.

TABLE 4

Assay to Quantitate Unreacted Alkylating Agent
The table below is an example of a standard curve from the assay for unreacted alkylating agent.

| | 0% | 0.5% | 1% | 2% | 3% | 4% | 5% |
|---|---|---|---|---|---|---|---|
| OD @ 570 | 0.919 | 0.707 | 0.556 | 0.363 | 0.274 | 0.241 | 0.088 |

| | OD @ 570 |
|---|---|
| Unreacted Alkylating agent | 0.7734 |

When the data above is plotted it provides a standard curve, and in a typical preparation, it can be estimated that under the experimental conditions of this example, between 0.4 and 0.5% propylene oxide remains unreacted in the alkylation solution.

TABLE 5

Moisture Content
The table below shows how the moisture content tends to increase as the tissue goes through the alkylation process (between 72–96 hours).

| Tissue | Moisture Content (%) |
|---|---|
| Untreated | 78.35 |
| NaOH | 87.33 |
| NaOH/PO | 89.28 |

TABLE 6

Denaturation Temperature
The table below indicates the manner in which the denaturation (shrink) temperature tends to decrease as the tissue goes through the alkylation process.

| Tissue | Denaturation temperature |
|---|---|
| Untreated | 65.1° C. |
| NaOH | 62.4° C. |
| NaOH/PO | 49.2° C. |

EXAMPLE 2

In Vivo Biocompatibility and Biostability Study of PO-Capped Bovine Pericardium

In this study, propylene oxide (PO) capped, non-crosslinked bovine pericardium was compared with glutaraldehyde (GA) crosslinked bovine pericardium in a subcutaneous animal model, in terms of inflammation, changes in physical property, and remodeling of implant matrix with the host tissue.

Preparation of PO Treated Tissue

Patches (approximately 4 cm×6 cm) of fresh bovine pericardium were first treated in 1N NaOH for one hour, followed by immersion 2–3 times in 4 L of 50 mM citrate buffer for 1 hour. The NaOH treated tissue was then put in large test tubes containing 100 ml of 0.2 M $NaHCO_3$ buffer at pH 10.5 and 2% propylene oxide. The tubes were gently shaken on an automatic rocker for 48 hours at room temperature. The tissue was thoroughly washed with saline to a pH level of 6.5–7.5, and then stored in 70% ethanol.

Preparation of GA Crosslinked Tissue

Glutaraldehyde (GA) crosslinked bovine pericardium patches are commercially available under the tradename "Peri-Guard", including Supple Peri-Guard™, and were obtained from Bio-Vascular, Inc., St. Paul, Minn.

Sterilization

The wet tissue patches were cut into a sample size of 1 cm×2 cm. The samples were laid flat on a plastic wrap (four each) and enclosed by folding the plastic wrap around. The wrapped samples were placed inside plastic/aluminum foil pouches that were subsequently purged with Argon gas and heat-sealed. The pouches were sent for sterilization by electron beam radiation at 25±2.5 KGy.

Implantation

The animals were 3 month old Fisher 344 male rats. Each animal received two different material implants. Upon the surgical procedures, the animals were anesthetized with pentobarbital (5 mg/100 g), and the upper backs were shaved and washed with a butadiene solution. A 2 cm incision was made over the midline on the back of the animal. The subcutaneous tissue plains were dissected laterally to form a pouch on the left and right sides of the back. One sample was inserted and spread flat in each pouch. Wounds were closed with surgical sutures and washed with butadiene. The animals were returned to their cages after recovering from anesthesia.

Explantation

At 4 and 12 weeks post-implantation, animals were sacrificed by carbon dioxide inhalation. The samples were retrieved together with the surrounding adherent tissue. The retrieved samples were cut in 3 pieces. One piece was stored in saline with 0.3% sodium azide and used for suture retention test, the second one fixed in Bouin fixatives and sent for embedding, sectioning and hematoxylin and eosin ("H&E") staining, and the third piece stored frozen and used for enzymatic digestion assays.

Suture Retention Measurement

A suture retention test that determines the force necessary to pull a suture loop from the prosthesis was performed on the ChemDyne MC1000 (Columbia Labs, Inc.) tensile testing system. A 5-0 Prolene suture was looped through the tissue with a 2 mm bite below the edge of the tissue. The suture loop was pulled at a rate of 100 mm/min with sampling rate of 20 Hz.

Enymatic Digestion Assays

The tissue samples were immersed in 1.0 ml of 40 U/ml collagenase (Worthington, Biochem Corp.) and 1.0 ml of 0.05% trypsin/EDTA solution, respectively. The samples were incubated for 12 hours at 37° C. and scored visually for tissue integrity.

Results

Suture Retention

While GA crosslinked bovine pericardium substantially maintained its suture retention property throughout the implantation period (up to 12 weeks after E-beam sterilization), there were substantial changes in the PO capped tissue following E-beam sterilization as well as implantation (Table 7). It appears that E-beam radiation reduced the suture retention of PO capped tissue by about 60%. The suture retention was further reduced during the implantation period. However, it is interesting that the suture retention of PO capped tissue appeared to increase with time after reaching the lowest level at 4 weeks post-implantation.

TABLE 7

Suture Retention Force (g) of Tissue Samples Before and After E-Beam Sterilization and Implantation in Rats

| Tissue Materials | GA Crosslinked (SPG) | PO Capped |
|---|---|---|
| Prior to E-Beam & Implantation | 1180 ± 50 (n = 4) | 802 ± 212 (n = 4) |
| Post E-Beam, Prior to Implantation | Not Tested | 300 ± 19 (n = 4) |
| 4 Weeks Post Implantation | 914 ± 173 (n = 4) | 82 ± 29 (n = 4) |
| 12 Weeks Post Implantation | 1039 ± 145 (n = 4) | 157 ± 39 (n = 4) |

Enzymatic Digestion

GA crosslinking rendered bovine pericardium resistant to collagenase and/or trypsin before and after implantation (up to 12 weeks). However, the PO capped bovine pericardium was readily digested by collagenase as well as trypsin prior to implantation. Since bovine pericardium is largely made of collagen that in its natural state (i.e., non-crosslinked) can be digested by collagenase but not trypsin, it is interesting that the tissue became susceptible to trypsin after PO capping. Following implantation, the PO capped samples were totally digestible by trypsin at 4 weeks, but partially at 12 weeks. It is possible that new collagen formed in the samples at later stages of implantation.

Histological Evaluation

The histological slides (H&E stain) were evaluated under an optical microscope and scored under a scale of 1 to 4 (Table 7). At 4 weeks post-implantation, the GA crosslinked samples induced a slight to moderate level of inflammatory response as characterized by considerable amounts of polymorphonuclear leukocytes (PMN's), macrophages, and foreign body giant cells, as well as lymphocytes, found mainly at the outer surfaces of the implant. In comparison, very mild or no reaction was found for the PO capped samples that looked clean with very few inflammatory cells present. Fibrous encapsulation was evident around the GA crosslinked tissue implants, but almost not detectable in PO capped samples. Collagen fiber structure in the GA crosslinked tissue matrix was unchanged, while the tissue matrix of PO capped implants appeared delaminated and loose.

At 12 weeks post-implantation, while the inflammatory response to the GA crosslinked tissue was similar to that at 4 weeks with little change in the physical integrity, there were marked changes in the PO treated samples. There were more cellular infiltrates (especially fibroblasts) around, as well as within, the PO treated tissue. The PO capped tissue matrix became uniform and anisotropic with no wavy fibrous structure as observed in regular bovine pericardium. In some regions under a thin fibrous capsule, the tissue matrix resembled the characteristics of developing granulation tissue with fibroblasts, neo-collagen and macrophages.

TABLE 7

Microscopic Evaluation (Scale of 1 to 4) of Explants at 4 and 12 Weeks

| Parameters | GA Crosslinked (4 Weeks) | GA Crosslinked (12 Weeks) | PO Capped (4 Weeks) | PO Capped (12 Weeks) |
|---|---|---|---|---|
| Polymorphoneuclear (PMNs) | 2 | 2 | 1 | 1 |
| Lymphocytes | 2 | 2 | 1 | 1 |
| Plasma Cells | 0 | 0 | 0 | 0 |
| Macrophages | 1 | 2 | 0 | 1 |
| Giant Cells | 2 | 2 | 0 | 1 |
| Necrosis | 0 | 0 | 0 | 0 |
| Fibroplasia | 0 | 0 | 0 | 0 |
| Fibrosis | 2 | 3 | 1 | 2 |
| Fatty Infiltrate | 0 | 0 | 0 | 0 |
| Fibroblast Proliferation | 0 | 0 | 1 | 2 |

In conclusion, compared with the GA crosslinked bovine pericardium, the PO capped, non-crosslinked bovine pericardium induced less inflammation as indicated by fewer inflammatory cells (such as PMNs and macrophages) present at 4 and 12 weeks post-implantation. While the GA crosslinked tissue maintained most of its physical and structural integrity throughout the implantation period, the PO capped tissue appeared to undergo significant changes during implantation. Following implantation, the PO capped tissue was partially degraded within the first few weeks resulting in decreases in suture retention. Interestingly, however, instead of being totally adsorbed in the body the material appeared to be remodeled over time with new host tissue and became stronger with increasing suture retention. New collagen formation probably occurred in the remodeling process as indicated by fibroblast proliferation and increased resistance of the explants to trypsin digestion at 12 weeks. Histological examination revealed that at later stages (e.g. 12 weeks) of implantation the matrix of PO capped bovine pericardium began to resemble the granulation tissue, which is the specialized type of tissue that is indicative of a normal healing process.

What is claimed is:

1. A surgical method comprising the steps of:
   providing a resorbable, remodelable implant material comprising a sterile, non-crosslinked, decellularized and purified mammalian tissue having a major percentage of its available amine groups alkylated; and
   implanting the implant material within the body, the material being adapted for use in a surgical application selected from the group consisting of duraplasty, thoracic, abdominal, urological, opthalmological, cardiac, and vascular surgery.

2. A surgical method according to claim 1 wherein the tissue is selected from the group consisting of serous and fibro-serous membranes.

3. A surgical method according to claim 2 wherein the tissue is selected from the group consisting of pericardium, peritoneum, fascia lata, dura mater, dermis and small intestinal submucosa.

4. A surgical method according to claim 3 wherein the tissue comprises bovine pericardium.

5. A surgical method according to claim 1 wherein the material has been alkylated by an alkylating agent selected from the group consisting of 1,2-epoxy-R compounds where R is an alkyl group up to 6 carbon atoms.

6. A surgical method according to claim 5 wherein the alkylating agent is propylene oxide.

7. A surgical method according to claim 5 wherein the alkylating agent is methyl glycidyl ether.

8. A surgical method according to claim 1 wherein the material is provided in the form of flat or textured sheets or strips.

9. A surgical method according to claim 1 wherein the step of providing a resorbable, remodelable implant material includes the steps of providing a biological tissue, treating the biological tissue with an alkylating agent under conditions suitable to alkylate a major percentage of available amine groups in the tissue, and sterilizing the treated tissue for use in vivo.

10. A surgical method according to claim 9 wherein the biological tissue is treated with a base prior to the alkylating step.

11. A surgical method according to claim 9 wherein the alkylating agent is used at a pH of between about 9 and about 11.

12. A surgical method according to claim 9 wherein the concentration of alkylating agent is between about 2% (v/v) and about 5% (v/v).

13. A surgical method according to claim 9 wherein the tissue is exposed to the alkylating agent for at least 48 hours.

14. A surgical method according to claim 1 wherein the step of implanting comprises implanting the material using a suture material.

15. A surgical method according to claim 14 wherein the step of implanting comprises implanting the material using a glue.

16. A surgical method according to claim 14 wherein the suture material is absorbable.

17. A surgical method according to claim 14 wherein the suture material is non-absorbable.

18. A surgical method according to claim 1 wherein the step of implanting comprises implanting the material and leaving the material in the body so that it is gradually remodeled or absorbed.

19. A surgical method according to claim 1 wherein the step of providing an implant material comprises providing implant materials prepared and packaged in various sizes.

20. A surgical method according to claim 1 wherein the step of providing an implant material comprises providing the implant material in a packaged form.

21. A surgical method according to claim 20 wherein the packaged form comprises an implant material packaged in a dehydrated condition.

22. A surgical method according to claim 21 further comprising the step of rehydrating the implant material packaged in a dehydrated condition prior to surgery.

23. A surgical method according to claim 1 wherein the step of providing an implant material comprises providing the implant material having a configuration and dimension adapted for use with a particular type of surgery.

24. A surgical method comprising the steps of:

providing a resorbable, remodelable implant material comprising a sterile, non-crosslinked, decellularized and purified bovine pericardium tissue having a major percentage of its available amine groups alkylated by an alkylating agent selected from the group consisting of 1,2-epoxy-R compounds where R is an alkyl group up to 6 carbon atoms; and implanting the implant material within the body, the material being adapted for use in a surgical application selected from the group consisting of duraplasty, thoracic, abdominal, urological, opthalmological, cardiac, and vascular surgery.

* * * * *